United States Patent [19]

Corso, Jr. et al.

[11] Patent Number: 5,259,393
[45] Date of Patent: Nov. 9, 1993

[54] GUIDEWIRE HAVING CONTROLLED RADIOPACITY TIP

[75] Inventors: Philip P. Corso, Jr., Davie; Henry W. Collins, Miami, both of Fla.

[73] Assignee: Cordis Corporation, Miami Lakes, Fla.

[21] Appl. No.: 882,580

[22] Filed: May 13, 1992

[51] Int. Cl.⁵ ............................................. A61B 5/00
[52] U.S. Cl. ........................................................ 128/772
[58] Field of Search .................... 128/657, 772; 604/95, 604/164, 280-285

[56] References Cited

U.S. PATENT DOCUMENTS

| | | | |
|---|---|---|---|
| 4,538,622 | 9/1985 | Samson et al. | 128/772 |
| 4,721,117 | 1/1988 | Mar et al. | 128/772 |
| 4,748,986 | 6/1988 | Morrison et al. | 128/772 |
| 4,763,647 | 8/1988 | Gambale | 128/657 |
| 4,813,434 | 3/1989 | Buchbinder et al. | 128/772 |
| 4,821,722 | 4/1989 | Miller et al. | 128/344 |
| 4,922,924 | 5/1990 | Gambale et al. | 128/772 |
| 5,063,935 | 11/1991 | Gambale | 128/657 |

FOREIGN PATENT DOCUMENTS 2180277 12/1988 Japan .
WO91/00051 1/1991 PCT Int'l Appl. .
WO91/14395 10/1991 PCT Int'l Appl. .

*Primary Examiner*—Max Hindenburg
*Attorney, Agent, or Firm*—Watts, Hoffmann, Fisher & Heinke Co.

[57] ABSTRACT

A guidewire having a controlled radiopacity at the guidewire's distal tip. A single spring mounted to the guidewire has one tightly coiled region and a second more loosely coiled less radiopaque region. The loosely coiled region may be coated with plastic to avoid any undesirable tactility of the guidewire's outer surface.

8 Claims, 2 Drawing Sheets

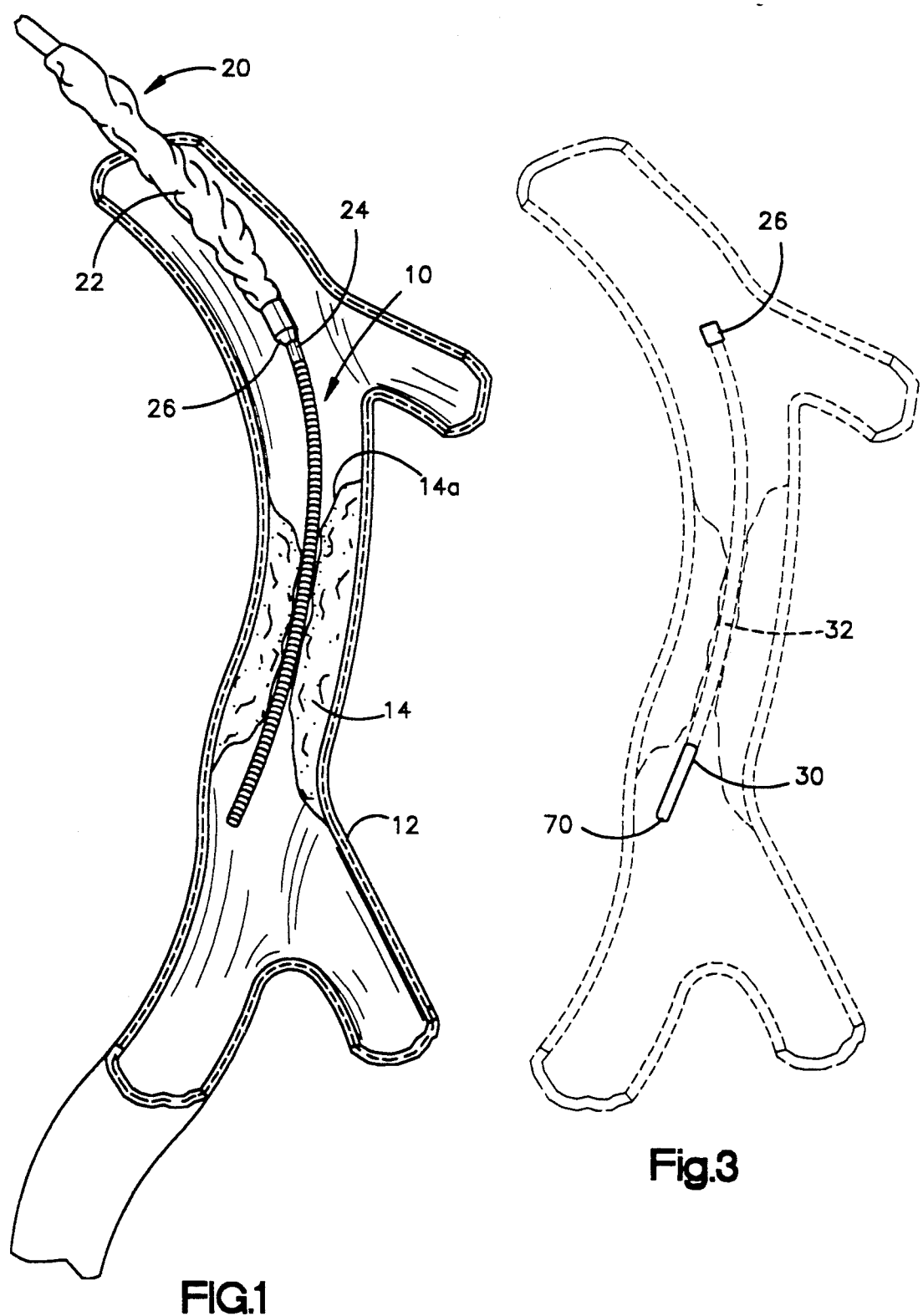

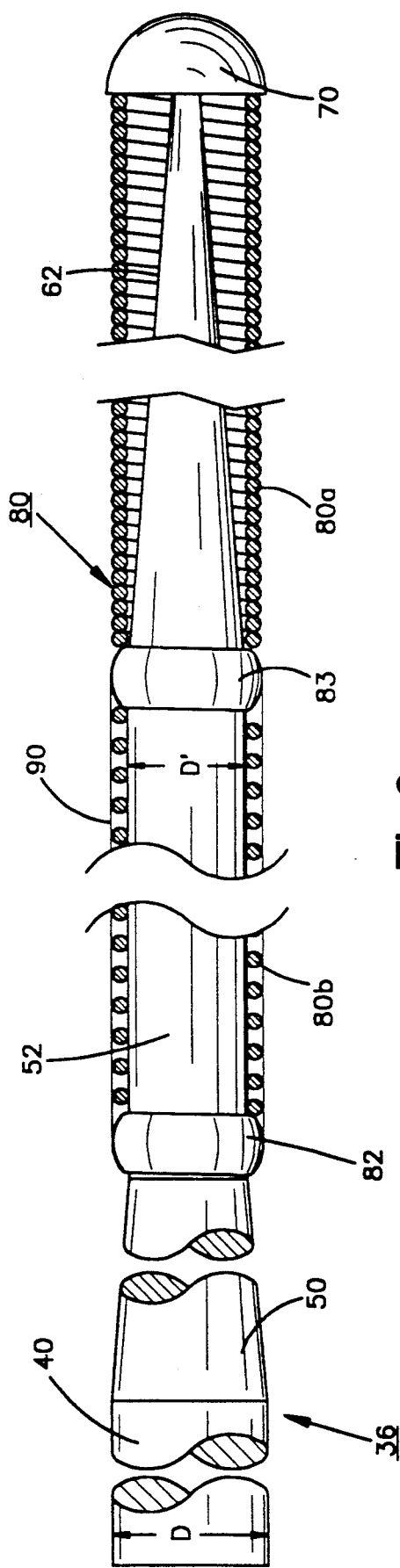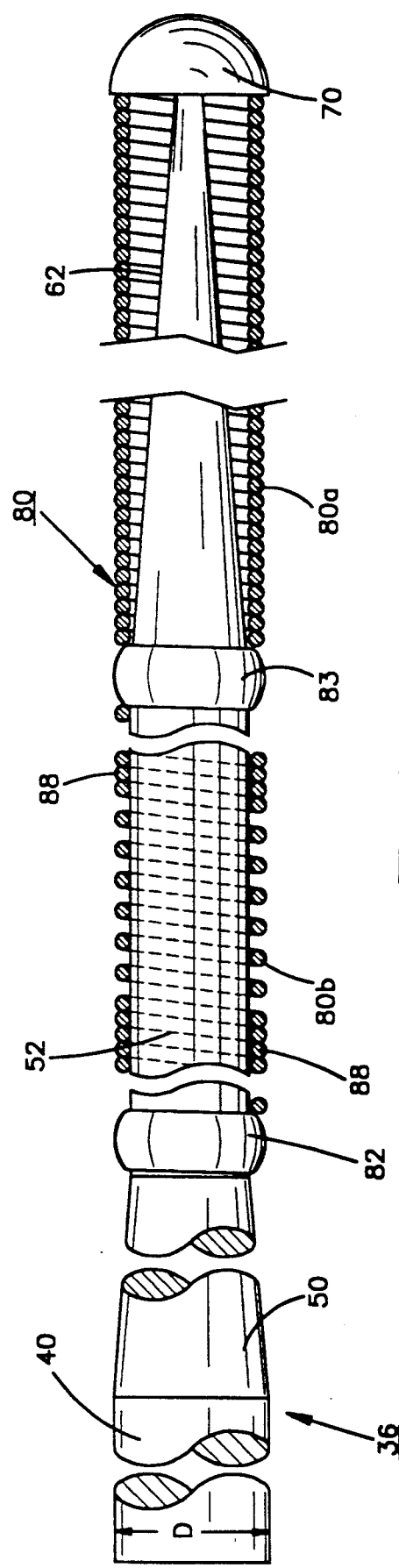

GUIDEWIRE HAVING CONTROLLED RADIOPACITY TIP

FIELD OF THE INVENTION

The present invention concerns a guidewire having controlled radiopaqueness at its distal end.

BACKGROUND ART

Percutaneous angioplasty is a therapeutic medical procedure that can increase blood flow through a blood vessel. It can sometimes be used as an alternative to coronary by-pass surgery, for example. An elongated catheter having a deflated balloon at its distal end is guided through a patient's cardiovascular system to the coronary artery of the heart. The balloon is inflated to compress deposits that have accumulated along the inner walls of the coronary artery to widen the artery lumen and increase blood flow.

A known technique for positioning the balloon catheter uses an elongated guidewire that is inserted into the patient and routed through the cardiovascular system as guidewire progress is viewed on an x-ray imaging screen.

Representative prior art patents that disclose flexible, elongated guidewires are U.S. Pat. No. 4,545,390 to Leary, U.S. Pat. No. 4,538,622 to Samson et al. and U.S. Pat. No. 3,906,938 to Fleischhacker and U.S. Pat. No. 4,846,186 to Box et al. The Box et al. patent is incorporated herein by reference.

One problem with currently available guidewires concerns the visibility of the guidewire. If the guidewire is fully opaque on a viewing screen, it can hinder viewing of post angioplasty angiograms used in studying the results produced by the angioplasty. Guidewires that have only an opaque tip do not adequately depict the arterial path on the viewing monitor.

U.S. Pat. No. 4,922,924 to Gambale et al. concerns a guidewire for use in placing a catheter. The guidewire includes a coil assembly that is formed from a highly radiopaque coil and a non-radiopaque coil, arranged in bifilar arrangement to define a moderate radiopacity guidewire section.

DISCLOSURE OF THE INVENTION

A variable radiopacity guidewire constructed in accordance with the invention includes an elongated corewire including a flexible, reduced diameter, distal corewire portion. A coiled wire spring is attached to the corewire and includes a first region of tightly spaced coils that define a highly radiopaque spring portion and a second region of more loosely spaced coils defining a less radiopaque spring portion. Distal and proximal ends of the coiled wire spring are attached to the corewire at a distal end of the guidewire.

The pitch or spacing of the loosely spaced coils can be adjusted to control the radiopacity of the guidewire's distal end. Less radiopacity under fluoroscopic examination is achieved without using a different spring wire material or the need to resort to two different spring wires.

The tactility of the spring along the loosely coiled region can be controlled by applying a plastic coating to fill in the gaps between adjacent coils. This can be accomplished by either drawing a sleeve over the coils and heat shrinking the sleeve in place or by dip or spray coating the plastic onto the guidewire.

These and other objects, advantages and features of the invention will become better understood from the detailed description of a preferred embodiment of the invention which is described in conjunction with the accompanying drawings.

BRIEF DESCRIPTION OF THE DRAWINGS

FIG. 1 is a diagrammatic view showing a blood vessel that has been occluded with deposits along an inner wall and shows the positioning of a flexible guidewire within the blood vessel;

FIG. 2 is an elevation segmented view of a flexible guidewire constructed in accordance with the invention; and FIG. 2A is a segmented view of a flexible guidewire with a plurality of tightly coiled regions.

FIG. 3 is a view of a flexible guidewire constructed in accordance with the invention as it appears when viewed on a fluoroscopic examining screen.

BEST MODE FOR CARRYING OUT THE INVENTION

Turning now to the drawings, FIG. 1 illustrates a distal portion of a flexible, small diameter guidewire 10 that can be guided through a patient cardiovascular system. A distal end of the guidewire is shown in FIG. 1 bridging a region in a blood vessel 12 having occlusions 14 which restrict blood flow through the blood vessel 12. The guidewire 10 is long enough to be routed from a patient entry point through the patient to the obstructed blood vessel region. In a preferred embodiment the guidewire has a length of 175 cm. (approximately 69 inches). As the guidewire 10 is inserted along the tortuous path to the obstructed blood vessel region, an attending physician conducting the procedure monitors progress of the guidewire 10 on a viewing screen.

The FIG. 1 depiction illustrates use of a guidewire for routing a balloon catheter 20 to the vicinity of the obstructions 14. The balloon catheter 20 includes a passageway or lumen that extends from a proximal location outside the patient to a distally located balloon 22. Fluid is routed into the catheter through this lumen to inflate the balloon 22. A distal tip portion 24 of the catheter 20 includes a marker band 26 to aid the attending physician in monitoring balloon catheter progress as it is positioned within the patient. A second, center passageway or lumen in the catheter 20 has a diameter sufficient to accommodate the guidewire 10 so that once the guidewire is properly positioned within the subject, the catheter 20 can be slid over the guidewire.

The distal tip portion of the guidewire 10 is flexible and can be bent to a predetermined configuration to facilitate routing the guidewire 10 along the cardiovascular system to the FIG. 1 region of the blood vessel 12. The pre-bent tip can be re-oriented by the physician. Torques applied to the proximal end of the guidewire are transmitted along the length of the guidewire and re-orient the distal tip to point in a desired direction.

In use, a distal end of the guidewire 10 is routed through a narrow passageway 14a in the obstruction 14 and the balloon catheter 20 slipped over the guidewire until the balloon 22 bridges the region 14 of obstructions within the blood vessel 12. The balloon 22 is then inflated and the balloon's outer surface contacts the obstruction 14. The inner walls of the obstruction 14 are compressed and a wider lumen or passageway created in the blood vessel 12.

As described in detail below, the guidewire 10 is constructed to include two sections 30, 32 (FIG. 3) of controlled radiopaqueness that appear when the blood vessel 12 is monitored on a viewing screen. The opacity of the sections 30, 32 can be varied and most preferably the opacity of the section 32 is less than the section 30. This allows adequate tracing of the guidewire while minimizing interference with a post procedure angiogram.

Turning now to FIG. 2, the guidewire 10 is seen to include a center stainless steel wire core 36 having a first or proximal uniform diameter portion 40 having a diameter D, in the range 0.010-0.038 inch, extending well over half the length of the guidewire. To improve the depiction of details of the distal portion of the guidewire 10, this uniform diameter elongated portion 40 has been sectioned and a major portion of its length deleted from FIG. 2.

The total length of the uniform diameter portion 40 is approximately 148 cm. of the total guidewire length of 175 cm. It is typically covered with a suitable coating to make its outer surface lubricious.

At the guidewire's distal end, the wire core 36 tapers along a segment 50 uniformly to a segment 52 having a uniform diameter D'. The corewire 36 again tapers uniformly along a segment 62 that has a length of approximately 1 inch and can be pre-bent to a particular configuration by the attending physician to facilitate insertion of the guidewire within the subject.

At the extreme distal tip portion of the guidewire 10, a weld 70 or other means of attachment such as brazing attaches a spring 80 to the corewire 36. The weld or braze 70 defines a smooth hemispherical bead which does not damage the inner lining of the blood vessels as the guidewire tip comes in contact with those linings.

The spring 80 is closely packed along the tapered core segment 62 so that adjacent coils 80a of the spring 80 are separated by a spacing or pitch distance of between 0.0005 and 0.002 inches with an optimum or preferred spacing of 0.001 inch. The coils 80b of the spring 80 overlying the uniform diameter segment 52 are less tightly packed with a controlled turn density to define gaps or spaces between adjacent coils. The coils 80b are spaced apart by between 0.003 and 0.006 inches with an optimum or preferred spacing of 0.005 inch (at least 1.5 times the spacing of coils 80a). A preferred spring is formed of coiled platinum wire having a diameter of 0.002 to 0.003 inches.

The spring 80 is soldered or brazed to the core 36 at two connections. One solder or braze connection 82 joins the proximal end of the spring 80 to the core. A second solder connection 83 joins the spring 80 to the corewire at a transition between tightly packed and spaced apart spring coils. The core 36 is constructed from a uniform diameter stainless steel wire which is centerless ground along the tapered segment 50 to the reduced diameter segment 52 and again ground along the tapered segment 62. A distal end of the tapered segment 62 may be flattened by rolling or stamping to increase the flexibility of the guidewire's tip.

The guidewire 10 depicted in FIG. 2 is particularly suited for insertion into small diameter blood vessels and can be used, for example, for positioning a balloon in a bridging relationship within the coronary artery.

FIG. 3 illustrates the image of the guidewire 10 which a physician would see while using the guidewire during angioplasty. Unlike a fully radiopaque guidewire, the visible band 30 is limited to the distal guidewire tip. The band 32 formed by the more loosely spaced spring coils is visible to aid the physician during the angioplasty but does not interfere with a post procedure angiogram. The winding density of the band 32 can be made more concentrated at equally spaced (one-half inch, for example) intervals 88 to provide a length reference for the physician when positioning the guidewire 10 within the blood vessel 12.

The exposed loosely wound coils of the spring 80 can optionally be covered with a plastic such as a suitable polymer. This can be accomplished by heat shrinking a sleeve 90 onto the spring 80, by dip coating of the spring into a suitable polymer coating bath, or by applying a spray coating of Teflon or the like.

The dimensions mentioned in this specification are for a preferred embodiment in the invention for use in small diameter blood vessels. These dimensions are representative of this use and are not intended to limit the invention, but rather define a small diameter guidewire whose characteristics are particularly advantageous. It is the intent, however, that the invention include all modifications and/or alterations from the disclosed dimensions and design falling within the spirit or scope of the appended claims.

We claim:

1. A controlled radiopacity guidewire comprising:
 a) an elongated corewire including a first, uniform diameter corewire portion and a second more flexible, reduced diameter corewire portion at one end of said corewire;
 b) a single coiled wire spring having distal and proximal ends attached to the corewire and including a first region of tightly spaced coils that define a high radiopaque distal spring portion and a second region of more loosely spaced coils defining a less radiopaque proximal spring portion;
 c) connection means for attaching the distal and proximal portions of the coiled wire spring to the corewire at spaced positions along the reduced diameter portion of the corewire and;
 d) a cover layer of plastic interconnecting loosely spaced coils of the less radiopaque proximal spring portion of said coiled wire spring.

2. The controlled radiopacity guidewire of claim 1 where the connection means additionally comprises:
 means for attaching the coiled wire spring to the corewire at a transition between the tightly spaced coils and more loosely spaced coils.

3. The controlled radiopacity guidewire of claim 1 where the single coiled wire spring includes multiple tightly coiled regions spaced apart at regular intervals to provide a length reference when viewed on a viewing screen.

4. The controlled radiopacity guidewire of claim 1 where the spacing between coils in the first region is less than or equal to 0.002 inches and the spacing between coils in the second region is equal to or greater than 0.003 inches.

5. A controlled radiopacity guidewire comprising:
 a) an elongated corewire including a flexible, reduced diameter, distal corewire portion;
 b) a single coiled wire spring having distal and proximal ends attached to the corewire and including a first region having a first pitch spacing between adjacent coils that define a high radiopaque spring portion and a second region having a second pitch spacing between coils greater than said first pitch spacing for defining a less radiopaque spring portion;

c) a first connector for attaching a distal end of the coiled wire spring to a distal end of the corewire and a second connector for attaching a proximal end of the coiled wire spring to the corewire; and d) a cover layer of plastic interconnecting spaced coils of the coiled wire spring along the second region of the coiled wire spring.

6. The controlled radiopacity guidewire of claim 5 additionally comprising:

a third connector for attaching the coiled wire spring to the corewire at a transition between the first and second pitch spacings between coils.

7. The controlled radiopacity guidewire of claim 5 where the single coiled wire spring includes multiple tightly coiled sections spaced apart at regular intervals to provide a length reference when viewed on a viewing screen.

8. The controlled radiopacity guidewire of claim 5 where adjacent coils in the first region are spaced apart by a pitch of 0.002 inches or less and adjacent coils in the second region are spaced apart by a pitch of 0.003 inches or greater.

* * * * *